(12) United States Patent
Nalin

(10) Patent No.: US 8,318,153 B2
(45) Date of Patent: Nov. 27, 2012

(54) METHOD OF MEDICALLY TREATING AN INDIVIDUAL

(76) Inventor: David R. Nalin, West Chester, PA (US)

( * ) Notice: Subject to any disclaimer, the term of this patent is extended or adjusted under 35 U.S.C. 154(b) by 497 days.

(21) Appl. No.: 11/478,070

(22) Filed: Jun. 29, 2006

(65) Prior Publication Data

US 2008/0003231 A1    Jan. 3, 2008

(51) Int. Cl.
*A61K 35/14* (2006.01)
*A61K 39/00* (2006.01)

(52) U.S. Cl. ............ 424/93.7; 424/93.71; 424/529
(58) Field of Classification Search ............ 424/93.7, 424/93.71, 529
See application file for complete search history.

(56) References Cited

U.S. PATENT DOCUMENTS

| 5,766,581 A * | 6/1998 | Bartley et al. ............ 424/85.1 |
| 6,261,839 B1 * | 7/2001 | Multhoff et al. ............ 435/373 |
| 6,407,218 B1 | 6/2002 | Tamarkin et al. |
| 6,528,051 B2 | 3/2003 | Tamarkin et al. |
| 6,716,422 B1 * | 4/2004 | Gajewski et al. ............ 424/85.2 |
| 2003/0026790 A1 * | 2/2003 | Hwu et al. ............ 424/93.21 |

OTHER PUBLICATIONS

Sengar et al. (1968) Can. J. Comp. Med., vol. 32, 593-597.*
Dos Santos (1977) J. Clin. Pathol., vol. 33(3), 288-289.*

* cited by examiner

*Primary Examiner* — Anne Marie S Wehbe
(74) *Attorney, Agent, or Firm* — James Ray & Assoc

(57) ABSTRACT

A method immunizing an individual that minimizes the amount of antigen or attenuated organism needed and the number of doses and clinic visits required, while making possible polyvalent simultaneous immunizations. The method comprises the steps of obtaining a sample of blood. Exposing at least a portion of this sample to at least one immunogenic antigen, attenuant or other immunogen. Incubating the exposed sample under specified optimal conditions and introducing this exposed sample into the individual to effect immunization thereof. The method of the invention also provides a method of delivery of materials, other than antigens, throughout an individual's body such as therapeutic drugs, virus vectors, genes, DNA, RNA, isotopes, and other therapeutic substances. A method for the delivery of treatment material to an individual is also provided by this method.

7 Claims, 1 Drawing Sheet

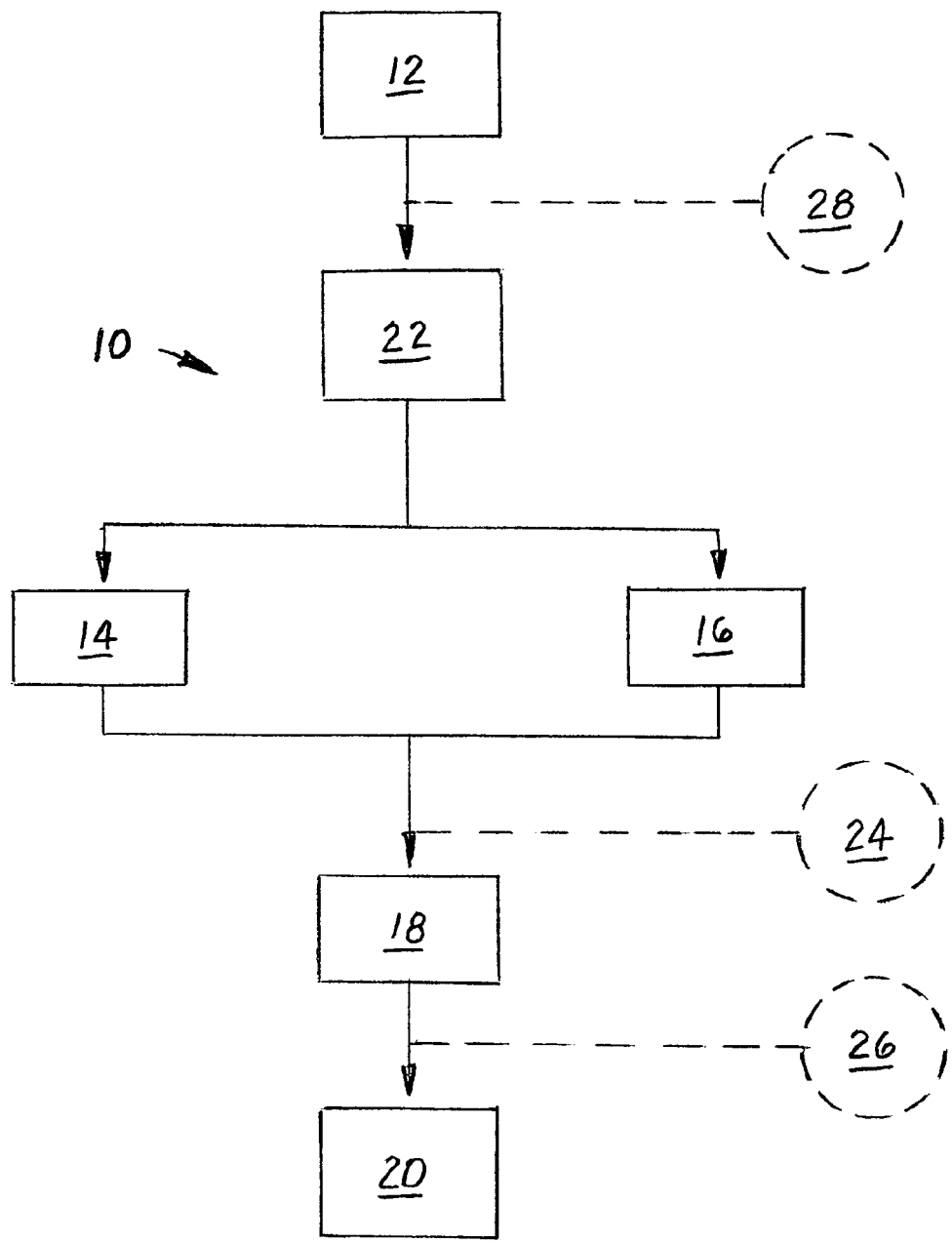

METHOD OF MEDICALLY TREATING AN INDIVIDUAL

FIELD OF THE INVENTION

The invention relates, in general, to a method of immunizing or treating an individual or an animal and, more specifically, to a method of immunizing or treating an individual or an animal through the use of an immunogenic antigen exposed blood sample.

BACKGROUND OF THE INVENTION

Immunization of individuals has long been a known technique for controlling diseases such as measles, mumps, rubella, polio, hepatitis and, more recently, chicken pox. Conventional immunizations deliver either an attenuated live strain of a pathogen or a killed organism or an immunogenic antigen derived from the targeted pathogen or its products, or one produced using recombinant genetic technology. Classical immunization delivers the vaccine by injection or by the enteric route. This approach is very indirect, requiring the antigen to be taken up by immunocytes before or after dispersion from the injection site to the surrounding tissue. The immunocytes then migrate to lymphatic nodes or spleen where antigen processing continues, or, for live vaccines, where the attenuated vaccine strain organisms multiply and are disseminated from. Exposure of immunocytes to the antigens or the attenuated pathogens triggers humoral and cellular mediated immune responses, which lead to absorption of antigens or elimination of attenuants followed by long lasting protection from disease caused by the respective pathogen(s).

The enteric route requires that the antigen or organism survive the numerous barriers posed by the gastric acid, digestive enzymes, competing microorganisms and biologically active lumenal or tissue substances, to reach a site from which the antigen or attenuated organism or products derived from an organism can be absorbed and can stimulate the immune system inducing a protective response. Other approaches, such as anti-idiotype immunization, or DNA injection, have been proposed but have not yet proven efficacious or safe in humans.

The routes of immunization for conventional vaccines have been parenteral (intramuscular, subcutaneous or intradermal) or oral/enteric. Evidence exists that other routes (rectal, aerosol/nasal, dermal, etc.) could be used, but various practical and safety limitations have blocked widespread applications via these routes. Direct administration of vaccines via the intravenous route has been avoided due to the possible risk of severe systemic allergies (anaphylaxis) in sensitive individuals, or the risk of embolization of vaccine components or of air.

In any case, all routes to date are modeled on the existing concept of multiple vaccinations, using individual (monovalent) or combination (polyvalent) vaccines. A reduction in the total doses needed for parenteral vaccines has been limited by the lack of lasting immune responses after only one dose of some vaccines, by interference between antigens when combined, and sometimes by safety or stability issues.

The expense of and barriers to vaccination are aggravated not only by the growing number of vaccines, doses, clinic visits for vaccinations, etc., but the need to manufacture multiple formulations free from adventitious organisms, noxious ingredients and/or contaminants or impurities. Additionally, the necessity of cold chain maintenance for many vaccines raises another barrier against vaccination in remote and impoverished areas. Also, relatively large volumes and large doses of most current vaccines are needed to ensure that some of the vaccine is injected into areas where it will come into contact with immunocytes within tissue, and to generate responses of protective magnitude.

Due to the increasing number of vaccines being introduced for disease control, an additional series of problems have arisen with the use of conventional vaccines. These problems include:
(a) Excessive expense for the vaccine products, vaccine administration, storage and clinic/office visits.
(b) Problems of compliance with costly and complex vaccination schedules.
(c) Unavailability of certain vaccines in impoverished areas.
(d) Growing dependence on health care workers for delivery of the vaccines.
(e) Lack of health care workers in many areas.
(f) Multiplicity of injections with complex schedules and injection site discomfort.
(g) Interference between certain antigens in polyvalent vaccines.
(h) Age restrictions for some vaccines.
(i) Production and supply limitations with frequent shortages.
(j) Safety concerns.

In view of the multiplicity of concerns associated with the administration of conventional vaccines, there is a need in the art for a new and revolutionary method of immunizing individuals, both humans and animals, which mitigates the problems enumerated above.

OBJECTS OF THE INVENTION

It is therefore an object of the invention to provide a method of immunization that minimizes the amount of antigen, attenuant or other immunogen needed and the number of doses and clinic visits required, while making possible polyvalent simultaneous immunizations.

It is a further object of the invention to provide a method of immunization that reduces the costs of immunization by reducing dose quantity, number of doses needed, number of visits needed, and degree of cold chain dependence of the vaccine.

It is another object of the invention to provide a method of immunization through the use of whole blood or buffy coat cells.

It is a further object of the invention to provide a method of delivery of materials, in addition to antigens, or attenuants, throughout an individual's body such as therapeutic drugs, virus vectors, genes, DNA, RNA, isotopes, and other therapeutic substances.

In addition to the various objects and advantages of the invention which have been described in some specific detail above it should be noted that various other objects and advantages of the present invention will become more readily apparent to those persons who are skilled in the relevant art from the following more detailed description, particularly, when such description is taken in conjunction with the attached drawing FIGURES and with the appended claims.

SUMMARY OF THE INVENTION

Briefly, and in accordance with the forgoing objectives, the invention provides a method immunizing an individual that minimizes the amount of antigen or attenuated organism needed and the number of doses and clinic visits required, while making possible polyvalent simultaneous immunizations. The method comprises the steps of obtaining a sample of blood. Exposing at least a portion of this sample to at least one immunogenic antigen, attenuant or other immunogen. Incubating the exposed sample for a predetermined amount of time and under specified optimal conditions of temperature, pH, ionic and nutrient environments and introducing this exposed sample into the individual to effect immunization thereof. The method of the invention also provides a method of delivery of materials, other than antigens, throughout an individual's body such as therapeutic drugs, virus vectors, genes, DNA, RNA, isotopes, and other therapeutic substances. This method comprises the steps of obtaining a sample of blood, exposing at least a portion of this sample to at least one of the treatment agents mentioned above, incubating the exposed sample for a predetermined amount of time and under specified optimal conditions of temperature, pH, ionic and nonionic nutrient environments and introducing the exposed (incubated) sample into the individual to effect treatment thereof.

BRIEF DESCRIPTION OF THE DRAWING

The FIGURE shows a block diagram depicting the steps for immunization and/or treatment of an individual according to the invention.

DETAILED DESCRIPTION OF THE INVENTION

Prior to proceeding to a more detailed description of the invention, it should be noted that identical components having identical functions have been designated with identical reference numerals for the sake of clarity. Reference is now made to the FIGURE, which shows a block diagram, generally indicated as 10, depicting the steps for immunization and/or treatment of an individual according to the invention. The term "individual" is meant to include both humans and animals as the present invention may be used as a method of immunization and/or treatment of either people or animals. The method comprises the steps of obtaining a sample of blood 12. The step of obtaining a sample of blood can comprises any well-known technique, such as inserting a needle in the individual's blood vessel and withdrawing blood therefrom. Alternatively, a sample of blood may be obtained by one of obtaining cord blood cells and/or stem cells harvested from cord blood from a source compatible with the individual and compatible cells grown in a tissue culture or harvested from stem cells and/or cord blood cells.

Once this sample is obtained, the next step of the invention comprises exposing at least a portion of this sample to at least one immunogenic antigen, attenuant or other immunogen 14. Alternatively, this method may be used as a method of delivery of materials, other than antigens, throughout an individual's body 16. In this case, at least a portion of this sample may be exposed to therapeutic drugs, virus vectors, genes, DNA, RNA, isotopes, and other therapeutic substances.

The method of the invention can include the additional step of exposing the sample of blood to an anticoagulant agent 28.

The next step of the invention comprises incubating the exposed sample for a predetermined amount of time and under specified optimal conditions of temperature, pH, ionic, nonionic, and nutrient environments 18. The final step of the invention is to introduce this exposed (incubated) sample 20 into the individual to effect immunization and/or treatment thereof.

The method of immunizing an individual consists of exposing either an individual's whole blood (anticoagulated) or the buffy coat from such individual's anticoagulated blood sample directly to an immunogenic antigen or multiple such antigens, attenuants and other immunogens, and after an incubation period, reinjecting the exposed material back to the individual by injections, either by intravenous, intramuscular, subcutaneous, and intradermal injection. Alternatively, the exposed material may be reintroduced into the individual by an oral, gingival, or enteric route.

In order to obtain the buffy coat from the sample of blood, the method can include the step of centrifuging the sample to obtain the buffy coat 22. This buffy coat may be exposed to multiple immunogenic antigens, attenuants or other immunogens so that multiple immunizations may be accomplished with a single buffy coat sample.

As a variation on this method, in some situations it is anticipated that the in vitro incubation with immunogenic antigens, attenuants or other immunogens can be done using nonautologous compatible cells capable of inducing protective immune responses in the recipient. Additionally, the use of cord blood cells and stem cells harvested from cord blood or from tissue cultured cells or other compatible sources may be used.

Incubation of the immunocytes with antigens, attenuants or other immunogens could be accomplished using appropriate plastics, for example plates with wells coated with the vaccine antigen(s) into which immunocyte aliquots could be placed and, after incubation for a suitable interval, drawn out for reintroduction back into the done individual by the various techniques discussed above. By this technique, multiple cell sample aliquots can be exposed to multiple vaccine antigens and can be combined into a single cell injection preparation and applied to an individual via a single injection device.

The sample cell aliquots could, if need be, washed in vitro prior to 24 and/or following 26 the incubation with vaccine antigen, attenuant or other immunogen. This may offer the advantage of removing interfering antibodies and/or excess antigens, attenuants, proteins, nucleic acids, genes, interfering material, excipients, stabilizers, and preservatives.

The present invention suggests the possibility of multiple birth vaccinations, which would only be limited by the degree of responsiveness and maturity of the newborn's immune system with respect to particular vaccine antigens, non-living or living.

The method of the invention permits more direct contact between immunogenic antigen (or attenuated live microbes) than classical methods, which should permit immunization with minute quantities of vaccines, leading to cost savings and greater yield in terms of vaccinations per gram of vaccine produced. It is anticipated that vaccines of high purity will afford an advantage, and that purification procedures to produce such vaccines may need to be developed when sufficiently pure vaccines are not yet developed or marketed.

This method is also designed to permit contact between immunocytes in blood, either whole blood or the buffy coat, and multiple antigens. This should result in the requirement of less antigen or attenuant microbe and fewer doses to immunize, resulting in multiple immunizations in one procedure at one visit.

As discussed above, the method of the invention may also be used for distributing a treatment agent throughout an individual's body, both human and animal. This method is similar to the method of immunizing an individual except that instead of exposing the sample of blood to an immunogen 14, it is exposed to a treatment material 16. Once exposed to the treatment material, this sample is incubated 18 for a predetermined amount of time and under specified optimal conditions of temperature, pH, ionic, nonionic, and nutrient environments. After incubation, the exposed sample is reintroduced 20 into an individual to effect treatment thereof. This treatment agent may be any well-known treatment agent such as one of therapeutic drugs, virus vectors, genes, DNA, RNA, isotopes, and other therapeutic substances.

The additional steps of centrifuging the sample 22 to obtain a buffy coat, exposing the sample to an anticoagulant agent 28, washing the sample 24, 26 and the various reintroduction techniques into the individual 20 are discussed in detail above in relation to the immunization method. This method also allows for the exposure of the sample to multiple treatment agents and the reintroduction into the individual by means of a single injection device.

The method of the invention may also be used as a method of treating an individual for AIDS and other infectious disorders. This method comprises the steps of obtaining a blood specimen from the individual. Harvesting a buffy coat from the blood specimen. Exposing cells, including but not limited to CD8 cells, in the buffy coat to substances which can strengthen their response to pathogens or can induce the cells to multiply after reintroduction into the individual. The final step of the invention comprises reintroducing the exposed cells into the individual for treating one of AIDS and other infectious disorders. The step of reintroducing the exposed cells into the individual can comprise any well known technique such as injection, oral, enteric routes, and the like.

The invention has been described in such full, clear, concise, and exact terms so as to enable any person skilled in the art to which it pertains to make and use the same. It should be understood that variations, modifications, equivalents and substitutions for components of the specifically described embodiments of the invention may be made by those skilled in the art without departing from the spirit and scope of the invention as set forth in the appended claims. Persons who possess such skill will also recognize that the foregoing description is merely illustrative and not intended to limit any of the ensuing claims to any particular narrow interpretation.

I claim:

1. A method of vaccinating an individual prevention of a disease, said method comprising the steps of:
   (a) obtaining a sample of blood;
   (b) centrifuging said sample of blood to obtain a buffy coat of said blood;
   (c) exposing said buffy coat to at least one immunogenic antigen, multiple antigen, attenuated organism or other immunogen associated with said disease;
   (d) incubating said exposed buffy coat for a predetermined amount of time and under specified optimal conditions of temperature, pH, ionic and nutrient environments; and
   (e) introducing said buffy coat into said individual to effect vaccination thereof, wherein said step of introducing said exposed buffy coat into said individual comprises one of i) injecting said exposed buffy coat by one of intravenous, intramuscular, subcutaneous and intradermal injection or ii) an oral or gingival application; and wherein said exposed buffy coat is not irradiated.

2. A method of vaccinating an individual as recited in claim 1 including the additional step of exposing said sample of blood to an anticoagulant agent.

3. A method of vaccinating an individual as recited in claim 1, wherein said step (c) includes exposing said buffy coat to multiple immunogenic antigens, attenuated organisms or other immunogens associated with said disease.

4. A method of vaccinating an individual as recited in claim 1 wherein said step of obtaining a sample of blood comprises inserting a needle in a blood vessel of said individual and withdrawing said blood therefrom.

5. A method of vaccinating an individual as recited in claim 1 wherein said individual comprises one of a human and non-human animal.

6. A method of vaccinating an individual as recited in claim 1 wherein said step of exposing said buffy coat to at least one immunogenic antigens, multiple antigen, attenuated organism, or other immunogen includes exposing said buffy coat to said at least one immunogenic antigen, multiple antigen, attenuated organism, or other immunogen within a single injection device.

7. A method of vaccinating an individual as recited in claim 1 including the step of washing said buffy coat in vitro prior to and/or following said incubation step to remove at least one of interfering antibodies, excess antigens, attenuants, proteins, nucleic acids, genes, interfering material, excipients, stabilizers, and preservatives.

* * * * *